(12) United States Patent
Muccini et al.

(10) Patent No.: US 6,552,791 B2
(45) Date of Patent: Apr. 22, 2003

(54) NONDESTRUCTIVE APPARATUS AND METHOD FOR DETECTING MOLECULAR ORIENTATION IN THIN FILMS

(75) Inventors: Michele Muccini, Bologna (IT); Carlo Taliani, Bologna (IT)

(73) Assignee: Consiglio Nationale Delle Ricerche, Rome (IT)

( * ) Notice: Subject to any disclaimer, the term of this patent is extended or adjusted under 35 U.S.C. 154(b) by 229 days.

(21) Appl. No.: 09/741,353

(22) Filed: Dec. 21, 2000

(65) Prior Publication Data

US 2001/0007500 A1 Jul. 12, 2001

(30) Foreign Application Priority Data

Dec. 27, 1999 (IT) .......................................... MI99A2718

(51) Int. Cl.$^7$ .............................................. G01N 21/25
(52) U.S. Cl. .......................... 356/417; 435/4; 356/364; 250/341.1
(58) Field of Search ................................. 356/364–370, 356/450–456, 416–420; 250/340–341.7; 435/4, 6

(56) References Cited

U.S. PATENT DOCUMENTS

| | | | |
|---|---|---|---|
| 4,264,207 A | * | 4/1981 | Batyrev et al. .............. 356/364 |
| 4,521,111 A | * | 6/1985 | Paulson, Jr. ................. 356/367 |
| 4,651,011 A | | 3/1987 | Ors et al. |
| 5,215,883 A | * | 6/1993 | Chu .............................. 435/6 |
| 5,365,067 A | | 11/1994 | Cole et al. |
| 5,532,488 A | * | 7/1996 | Ishibashi et al. ......... 250/341.3 |
| 5,598,005 A | | 1/1997 | Wang et al. |
| 6,151,115 A | * | 11/2000 | Naulleau ..................... 356/354 |

OTHER PUBLICATIONS

Feldmann J, Guss W, Lemmer U, Gobel E O, Taliani C, Mohn H, Muller W, Haussler P, and Ter Meer H–U: "Photoluminescence studies of C60 single crystals." Molecular Crystals and Liquid Crystals, vol. 256, 1994, pp. 757–762, XP001010830 Switzerland p. 758, line 15–line 24 p. 761, line 1–p. 762, line 20 figure 1.

* cited by examiner

Primary Examiner—Frank G. Font
Assistant Examiner—Willie Davis
(74) Attorney, Agent, or Firm—Guido Modiano; Albert Josif; Daniel O'Byrne

(57) ABSTRACT

A method and an apparatus for nondestructively detecting the orientation of anisotropic molecules in thin films and in molecular layers in general. The present invention is based on a single measurement of the non-polarized photoluminescence spectrum, in order to determine whether the molecules are orientated at right angles or parallel to the surface of the molecular layer, fabricated with any technique. The method is fast and noninvasive and can also allow to observe noninterferingly in real time during growth the orientation of the molecules in the film. The result of this real-time observation can be used to optimize the growth conditions of the film in order to achieve the intended molecular orientation.

14 Claims, 6 Drawing Sheets

LEGEND
A- LASER SOURCE
B- THICKNESS AND EVAPORATION RATE MONITORING SYSTEM
C- SPECIMEN HOLDER
D- SUBSTRATE
E- CRYOSTAT WITH HEATER AND TEMPERATURE SENSOR
F- COLLECTING LENS
G- FLOW OF MOLECULES
H- SHUTTER
I- KNUDSEN CELL
J- EVAPORATION CONTROL UNIT ETC.
K- OPTICAL FIBER IN VACUUM
L- OPTICAL FIBER
M- SPECTRUM ANALYZER
N- COMPUTER WITH USER INTERFACE

NONDESTRUCTIVE APPARATUS AND METHOD FOR DETECTING MOLECULAR ORIENTATION IN THIN FILMS

FIELD OF THE INVENTION

The present invention relates to a nondestructive apparatus and method for determining the molecular orientation and the orientation of the unit cell of organic systems which are anisotropic or have anisotropic behavior, and particularly in thin films.

BACKGROUND OF THE INVENTION

Over the past ten years, interest in organic materials (or organic molecules) has increased enormously in view of the prospect of developing a new generation of electronic and photonic devices based on said materials.

Examples of organic-based devices which are currently of great interest are thin-film transistors [1] and light-emitting diodes [2], but the application potential is extremely broad.

With respect to the conventional technology of inorganic semiconductors, such as silicon and gallium arsenide, organic molecular materials offer the fundamental advantage that they can be easily processed as thin films and therefore can be compatible with large area flexible substrates. Their thermal and mechanical stability is another characteristic that makes them excellent candidates for applications in optoelectronic devices.

It has been demonstrated that high control of molecular order in films is absolutely necessary in order to control the basic physical phenomena that determine the operation of optoelectronic devices. Furthermore, control of the orientation of highly anisotropic systems is important, since the optical and transport properties are significantly anisotropic along the various crystalline directions.

Various growth techniques (such as for example Langmuir-Blodgett, vacuum sublimation, supersonic beams, et cetera) have been proved to be suitable for growing monomolecular layers of an organic compound. In said ultrathin films, thickness is controlled on the magnitude order of one unit of molecular length.

Molecular orientation on the substrate depends not only on the intrinsic molecular properties and on intermolecular interactions but also on the nature of the molecule-substrate interaction and on the growth kinetics. Said kinetics is controlled by a series of experimental parameters, such as the growth rate, the temperature of the substrate, and the thickness of the film.

The absolutely critical dependence of structural order and molecular orientation on the growth conditions makes it indispensable, in order to obtain highly orientated organic thin films, to be able to simply and rapidly measure the orientation of the molecules in the film.

Furthermore, since the film may be subsequently manipulated in order to vary the molecular orientation and therefore the optoelectronic properties, the real-time noninterfering evaluation of said manipulation is useful both for quality and for process control.

Known methods for evaluating molecular orientation comprise anisotropy of ultrasonic speed, X-ray diffraction, optical double refraction, optical dichroism, small-angle light scattering [U.S. Pat. No. 4,264,207], polarized reflectance [U.S. Pat. 5,365,067], photoluminescence anisotropy, and polarized photoluminescence.

These techniques usually require complicated measurements and highly critical modeling. Specific technical skill and a long time for making the measurements are also necessary.

Photoluminescence anisotropy and polarized photoluminescence have been used in order to measure molecular orientation in thin films of polymers and in films of organic molecules [3, 4, 5].

Furthermore, measurement of photoluminescence intensity as excitation polarization varies is used to monitor molecular orientation in [U.S. Pat. No. 4,521,111].

However, prior to the present invention it was not known how to determine the molecular orientation in a film from a single non-polarized luminescence measurement.

The aim of the present invention is to overcome the drawbacks of currently known methods for determining molecular orientation in thin films, by providing a method and an apparatus for detecting the orientation of organic molecules in thin films by means of a simple and rapid measurement of nonpolarized luminescence and without critical modeling.

Another object of the present invention is to provide a method and an apparatus which allow to detect whether the molecules are orientated in a thin film parallel to the substrate or at right angles thereto without performing polarized photoluminescence or photoluminescence anisotropy measurements.

Another object of the present invention is to provide a method and an apparatus for monitoring in real time, during the growth or manipulation of the film, the molecular orientation in said film with respect to the substrate or surface of the film.

Another object of the present invention is to provide a method and an apparatus for monitoring molecular orientation in the film noninvasively and noninterferingly.

Another object of the present invention is to provide a method and an apparatus which allow to optimize in real time the growth conditions of the film, in order to obtain specific structural characteristics.

SUMMARY OF THE INVENTION

This aim and these and other objects which will become better apparent from the description that follows are achieved, according to the present invention, by means of a method which comprises the steps of a) stimulation of the luminescence of the molecular layer; b) measurement of the consequent nonpolarized luminescence spectrum; c) spectral and vibrational analysis of said luminescence spectrum in order to determine the orientation of the molecules.

Luminescence can be obtained with any method, particularly with photoluminescence excitation or with an electroluminescence excitation. For the sake of simplicity, but without intending to limit the invention, reference is made in the remainder of the description exclusively to photoluminescence.

The invention furthermore provides an apparatus for detecting noninvasively and noninterferingly and, if necessary, in real time during dynamic growth or manipulation phenomena, the orientation of the molecules according to the above method. Said apparatus comprises the following elements: a) an exciter source suitable to induce photoluminescence of the specimen; b) an optical system for collecting the photoluminescence generated by the specimen; c) an analyzer of photoluminescence spectra with appropriate optical and spectral characteristics; d) an interface with the user, suitable to indicate the orientation of the molecules, optionally providing the relative weights of the various orientations detected with respect to the dominant orientation. Conveniently, the apparatus according to the present invention furthermore comprises e) a system for varying in real time the growth or manipulation conditions, suitable to act according to the result of the determination of the molecular orientation and achieve specific structural characteristics.

The inventors of the present invention have in fact found that the orientation of the molecules on the substrate is revealed by measuring a nonpolarized photoluminescence spectrum and observing the active vibronic transitions.

DETAILED DESCRIPTION OF THE INVENTION

The invention is described with reference to FIGS. 1 to 6.

Figure 3:
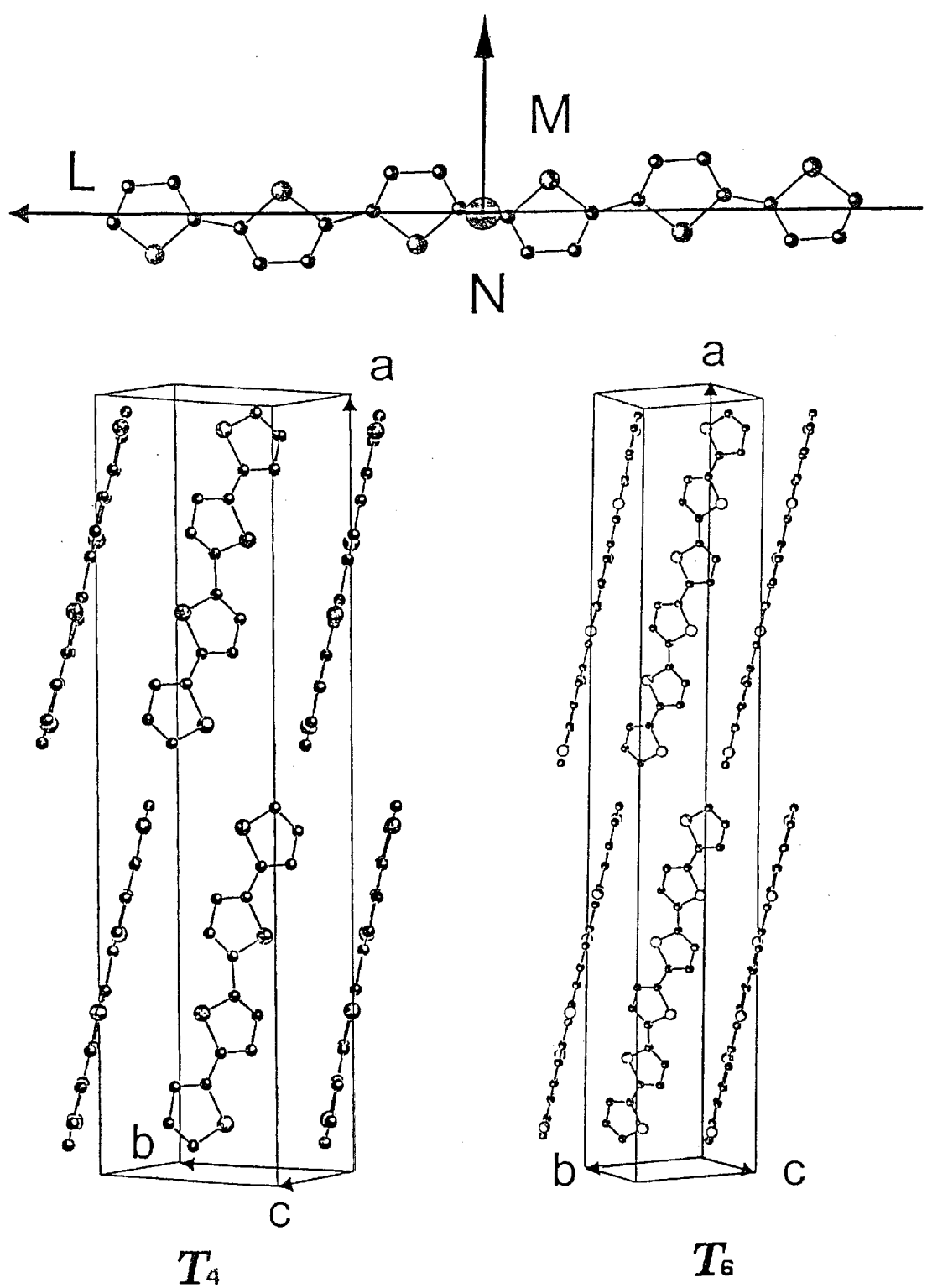

FIG. 3 plots the crystalline structure of the model system of the oligothiophenes, which are representative of the entire class of conjugated organic materials.

Figure 4:
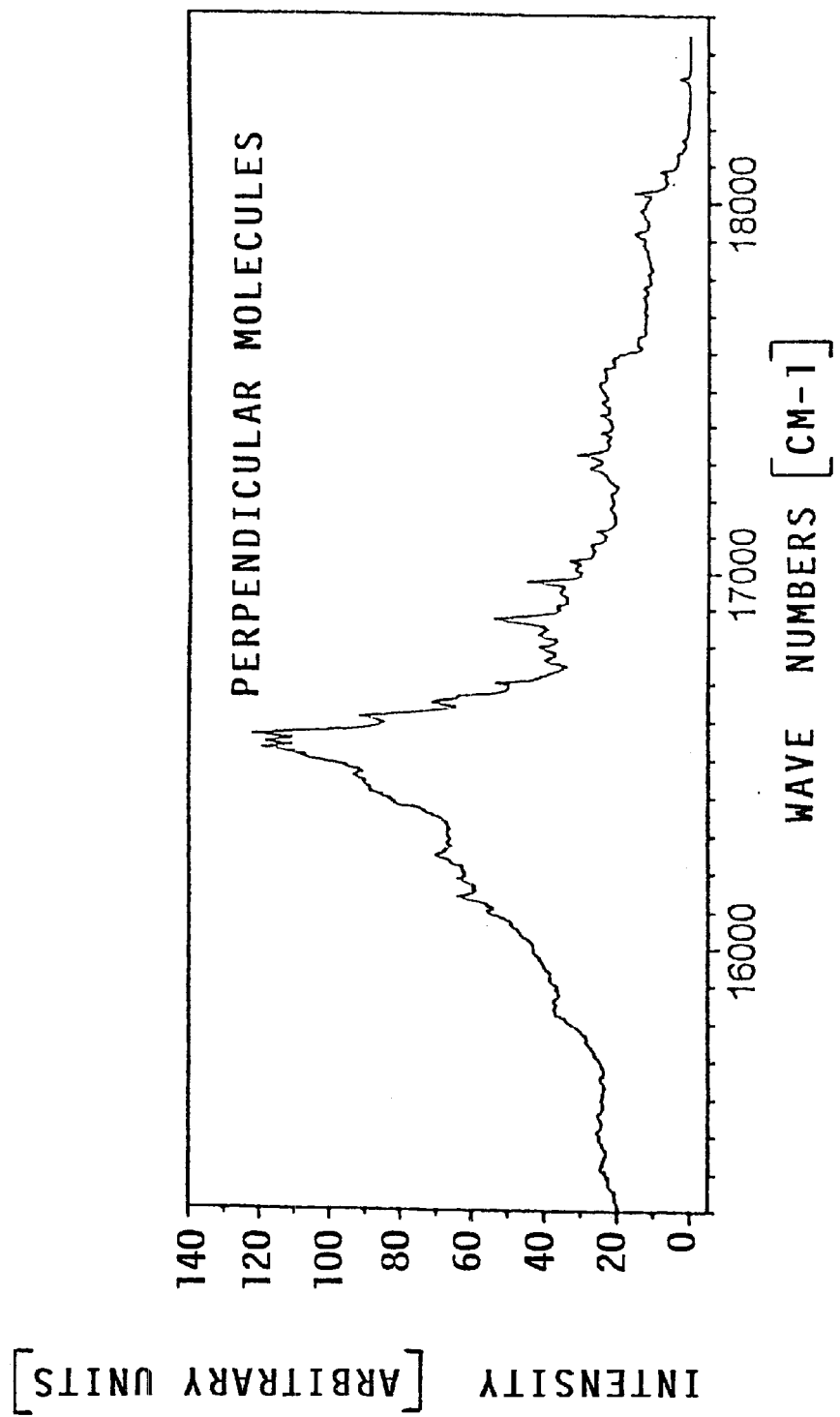

FIG. 4 plots the nonpolarized photoluminescence spectrum of a single hexathiophene crystal, in which the molecules are orientated at right angles to the lased surface.

Figure 5:
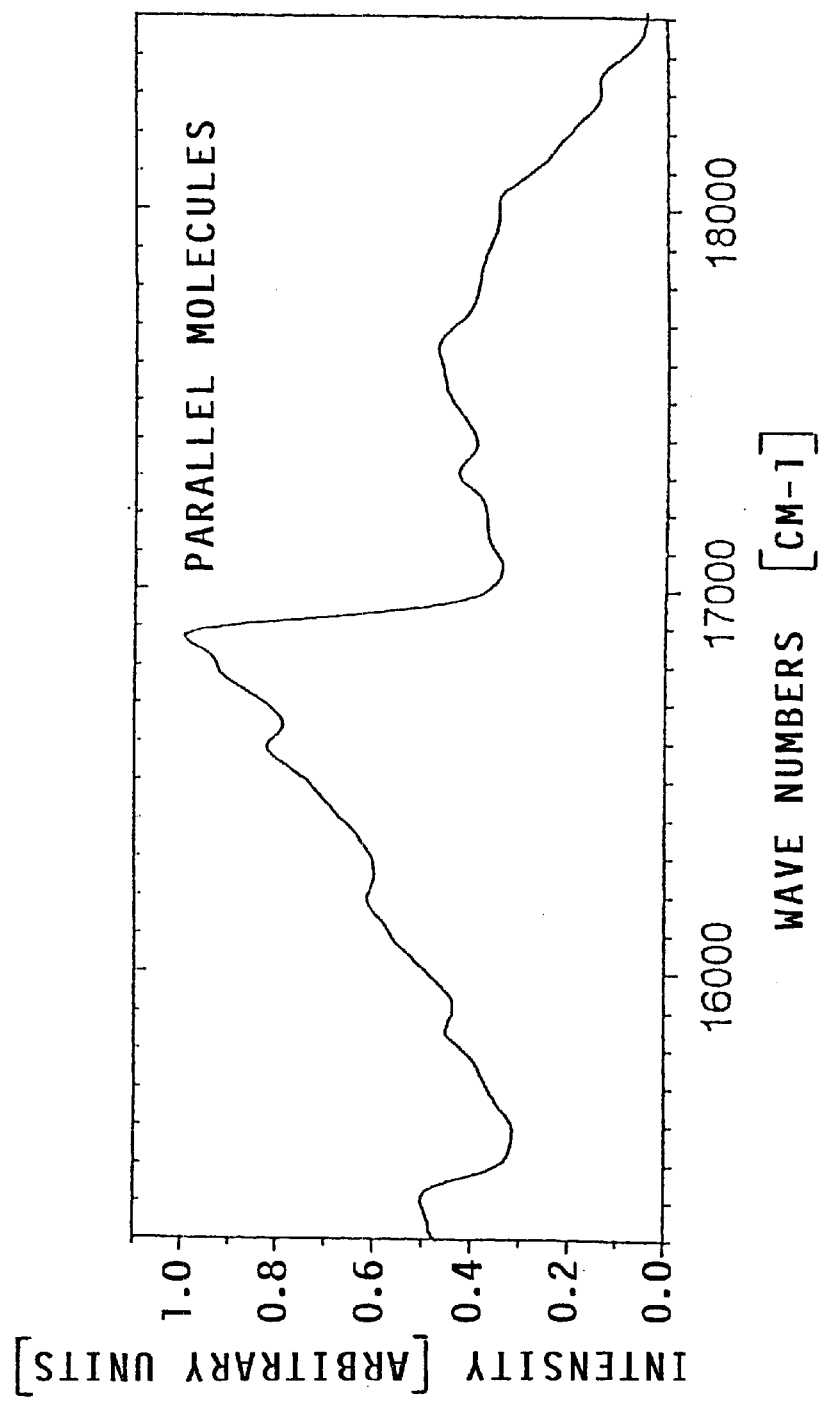

FIG. 5 plots the nonpolarized photoluminescence spectrum of an ultrathin film of hexathiophene on mica, in which the molecules are orientated parallel to the substrate.

Figure 6:
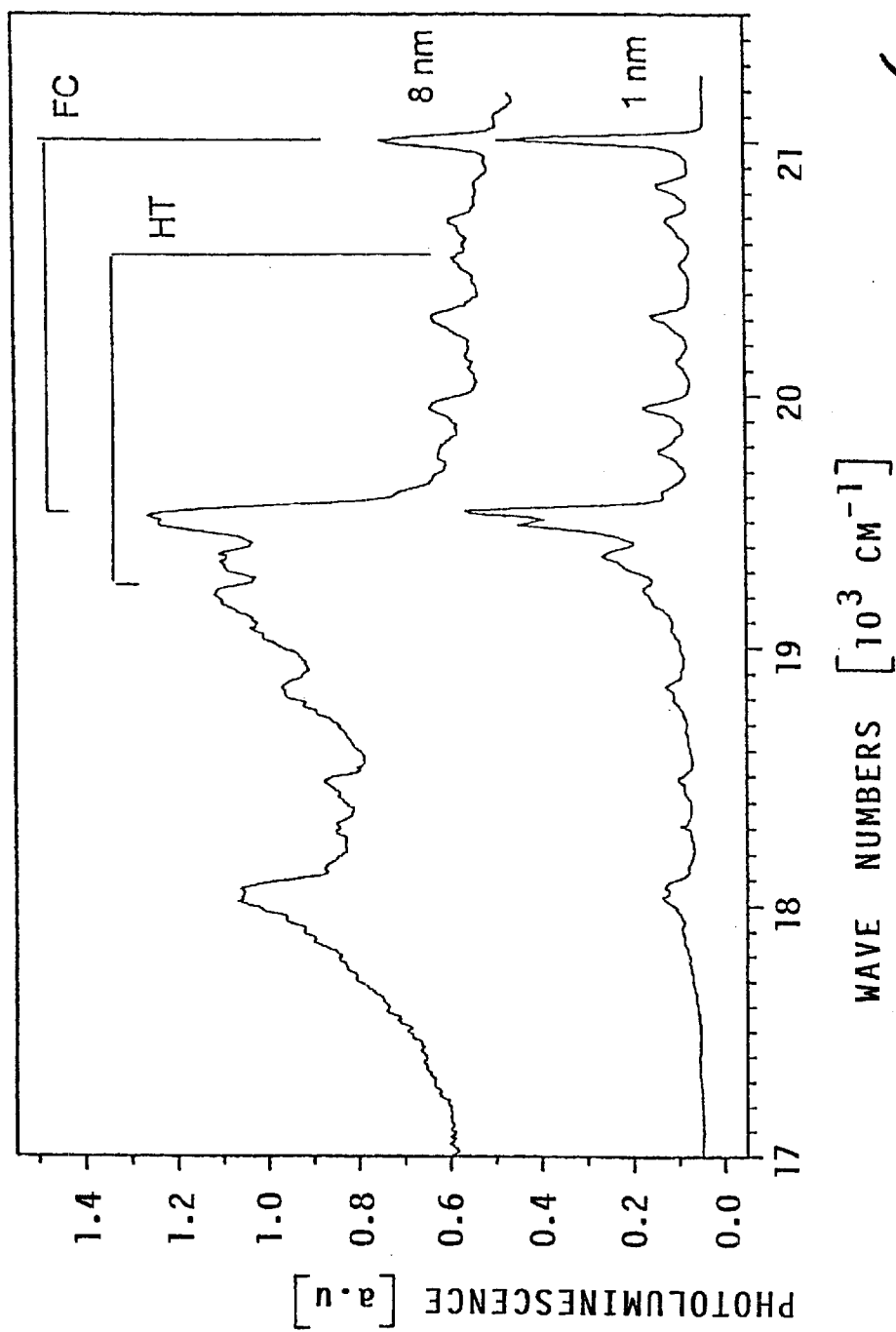

FIG. 6 plots the nonpolarized photoluminescence spectra of a tetrathiophene film on HOPG, measured during growth by sublimation in vacuum when the thickness of the film was respectively 1 nm and 8 nm. In the first case, the molecules are parallel to the substrate; in the second case, the molecules of the outermost layers are perpendicular to the substrate.

Although one does not wish to be constrained by any theory in particular, it is noted that when an electron of an organic molecule is excited from the fundamental state to high-energy excited electronic states it decays to the lower-energy excited electronic level without releasing photons. The lifetime of this excited state is typically on the order of one nanosecond.

If this excited state is radiatively coupled to the fundamental state (as occurs in all luminescent materials), the electron returns to the fundamental state, releasing its energy to photons which are emitted by the molecule (luminescence). The emitted photons have an energy which depends on the relative energy of the optically active excited electronic state with respect to the fundamental electronic state.

Furthermore, the purely electronic transition is coupled to vibrational modes of the fundamental electronic state of the molecule. This vibronic coupling induces the emission of photons with less energy than those produced by the fully electronic transition.

Vibronic transitions in the crystalline solid are polarized with respect to the crystalline faces and axes, so that in general the vibronic couplings with the electronic transition change according to the crystallographic observation perspective. Accordingly, one has a different photoluminescence spectrum depending on the crystalline face that is observed.

In the case of a thin film, the crystalline face that can be accessed for spectroscopic analysis changes if the molecules are upright or lie flat on the substrate.

In the case of the broad family of highly anisotropic conjugated organic systems ("rigid-rod" molecules, oligomers, polymers), the crystalline cell is in turn highly anisotropic. The long axis of the cell (see for example the axis a in FIG. 3, related to hexathiophene) is practically aligned with the molecule, while the other two axes (b and c in FIG. 3) are practically perpendicular to the molecule.

In the molecule, the optically active electronic transition with lower energy is polarized along the long axis of the molecule. At higher energies there are instead electronic transitions which are polarized at right angles to the long axis of the molecule and therefore project onto the crystalline plane bc.

The inventors of the present invention have noticed that all of the above conjugated organic systems tend to pack in the solid in a similar manner and that any variations in the herringbone angle and smaller or greater intermolecular interaction, despite changing the energy of the electronic transitions, do not alter for the purposes of the present invention the polarization properties of the vibronic transitions.

In general, the moment of vibronic transition between the excited electronic state $|\Phi_E\rangle$ and $|\Phi_G\phi_j\rangle$, where $\Phi_G$ and $\phi_j$ are the fundamental electronic state and the vibrational wave function, respectively, is defined as:

$$\mu = \langle \Phi_E | \mu(Q) | \Phi_G \phi_j(Q) \rangle \qquad (1)$$

Expanding the moment of electronic transition operator $\mu(Q)$ into a Taylor series into the normal nuclear coordinates around the equilibrium configuration $Q_O$, one obtains:

$$\mu(Q) = \mu(Q_0) + \Sigma_k (d\mu(Q)/dQ_k)_{Q0} Q_k + \qquad (2)$$

By substituting Eqn 2 in Eqn 1, one obtains the following expression for the vibronic transition moment:

$$\mu = \langle \Phi_E | \mu(Q_0) | \Phi_G \phi_j(Q) \rangle + \langle \Phi_E | \Sigma_k (d\mu(Q)/dQ_k)_{Q0} Q_k | \Phi_G \phi_j(Q) \rangle + \qquad (3)$$

The first term of Eqn 3 represents the Franck-Condon vibronic coupling in which the moment of electronic transition $\mu(Q)$ is independent of the nuclear coordinates and the polarization of the transition is the polarization of the electronic origin $|\Phi_E\rangle$. The second term of Eqn 3 represents the Herzberg-Teller (HT) vibronic coupling. The index k moves on the normal coordinates of the molecule, so that when the Condon approximation is relaxed, the moment of electronic transition becomes dependent on the nuclear coordinates. In the Herzberg-Teller mechanism, two electronic states couple by means of a molecular vibration. This vibration induces an oscillator force transfer from the higher-energy electronic state to the vibrational level of the lower-energy electronic transition. The polarization of said vibronic transition is the polarization of the higher-energy electronic level that releases oscillator force.

In the case of the above cited conjugated organic systems, HT transitions are polarized on the cristalline plane perpendicular to the molecular axis. The HT mechanism originates vibronic transitions which are present only on such plane and act as false electronic origins.

Accordingly, the photoluminescence spectrum changes radically depending on whether the crystalline face perpendicular to the molecular axis (the molecules are upright on the substrate) or the crystalline face which contains the molecular axis (the molecules are flat on the substrate) is observed.

The inventors of the present invention have devised a method and an apparatus for detecting the orientation of, molecules in a thin film on a substrate by measuring a nonpolarized photoluminescence spectrum and observing the active vibronic transitions.

With the method according to the present invention, vibrational analysis of nonpolarized photoluminescence spectra allows to recognize whether the molecules are perpendicular or parallel to the surface of the film by observing the presence, and possibly comparing the relative weights, of the vibronic transitions due to HT and FC mechanisms in the spectrum. If the spectrum is dominated by vibronic transitions constructed on false HT origins, the orientation of the molecules is predominantly perpendicular to the substrate, whereas if the spectrum is dominated by FC vibronic transitions constructed on the electronic origin, the molecules are predominantly parallel to the substrate.

Identification of the bands related to HT and FC vibronic transitions in nonpolarized photoluminescence spectra occurs by virtue of methods which ate known in the art.

Said bands can be identified, for example, on the basis of their position in the photoluminescence spectrum in the case of systems for which HT and FC transitions have already been preassigned.

In the case of systems for which prior vibrational analysis is completely unavailable, it is still possible to refer to the phonon mode which in conjugated organic systems couples most effectively with the lower-energy electronic transition. This phonon mode is due to the vibration of the double bond between carbon atoms and typically has an energy of $1470 \pm 50$ cm$^{-1}$ If the most intense peak in the photoluminescence spectrum is at this distance from the highest-energy peak in the spectrum (electronic origin), the molecules are parallel to the substrate. Vice versa, if the most intense peak in the spectrum is located at a greater distance from the electronic origin, the molecules are perpendicular to the substrate. In this case, too, the above remarks regarding the relative weights of the various components apply.

Accordingly, as a consequence of the present invention, it is no longer necessary, in order to know molecular orientation, to make measurements of polarized photoluminescence or photoluminescence anisotropy, as had been proposed. Rather, it is possible to detect whether the molecules are orientated parallel to the substrate or at right angles thereto by simply measuring a single nonpolarized photoluminescence spectrum.

In another aspect of the present invention, a method is provided for monitoring in real time during growth (for example by sublimation, supersonic beams, et cetera) the molecular orientation in thin films, said method comprising the stages of a) stimulation of photoluminescence by irradiation of the film with an exciter source; b) collecting the photoluminescence and measuring the spectrum with a spectrum analyzer whose spectral resolution and acquisition rate characteristics are suitable for real-time observation; c) automatic or operator-based analysis of the spectral and vibrational characteristics of the photoluminescence spectrum in order to deduce information on molecular orientation.

Said method allows to follow the evolution, over time, of the orientation of the molecules as the nominal thickness increases. The result of this real-time observation can be used to optimize the growth conditions of the film in order to obtain the intended molecular orientation, or in order to provide superstructures in which individual layers have different molecular orientations.

The methods of the present invention can be used to monitor in real time, or to detect ex post, the effect of manipulation or nanomanipulation, obtained in any way, on the molecular orientation in thin films.

The methods according to the present invention can furthermore be used to monitor the variation over time of the structural properties of films as a consequent of deterioration by aging, or due to operation in the case of optoelectronic devices based on said films.

In another aspect, the present invention provides an apparatus for detecting the orientation of anisotropic organic systems in thin films, comprising: a) a photonic source for inducing emission of photoluminescence of the film; b) a system of lenses which is suitable to effectively collect the luminescence of the film; c) a spectrum analyzer having spectral resolution and acquisition rate characteristics suitable for real-time observation; d) a user interface for reporting in real time the result of the monitoring of the molecular orientation. Conveniently, the apparatus according to the present invention furthermore comprises e) a system for the real-time variation of the growth conditions which acts automatically in relation to the result of the monitoring, or by performing the instructions of the operator.

The apparatus according to the present invention can furthermore comprise a system for focusing on the specimen the exciter source and/or a system for filtering the exciter source (for example a bandpass optical filter or a Notch filter) which eliminates the contribution of said source before the photons that arrive from the specimen and are channeled into the collection system are analyzed by the spectrum analyzer.

Necessarily, the photonic source has an energy and power which are appropriate for effectively stimulating the photoluminescence of the specimen without altering the optoelectronic and structural characteristics of the film.

When the apparatus according to the present invention is meant to be used to monitor in real time the molecular orientation or to monitor the effect of the manipulation on the molecular orientation, the exciter source has an incidence on the specimen at a preset angle so as be compatible with the physical dimensions and any movement of mechanical parts, so as to avoid interfering with any film growth or manipulation process, and in turn so as to avoid being interrupted in its path by said mechanical parts.

Advantageously, the collection of the photoluminescence and its channeling inside the spectrum analyzer can also be performed with low-loss optical fibers, allowing optimum spatial arrangement of the measurement components around the growth apparatus or the film itself.

Preferably, the interface with the user is suitable to provide the relative weights of the detected orientations, in terms of percentages with respect to the dominant orientation.

Advantageously, the apparatus according to the present invention also comprises a system for the real-time variation of the growth conditions which is suitable to act according to the result related to molecular orientation to achieve a growth target.

Furthermore, in the case of the manipulation of an already-formed film, the apparatus according to the present invention can comprise a system for the real-time variation of the manipulation conditions Which is suitable to act according to the result of the observation in order to achieve a manipulation target.

Moreover, the methods and the apparatus according to the present invention are understood to also apply to use for determining molecular orientation in layers of molecules even if they are not supported by a substrate.

The following examples are provided merely by way of non-limitative illustration of the invention.

EXAMPLES

By way of non-limitative example, examples related to oligothiophenes [6], a model system which has been studied extensively and whose structural and electronic properties can be easily and directly extended to the entire family of conjugated organic materials, are cited.

Example 1

A single crystal of hexathiophene obtained by sublimation in a controlled atmosphere of argon, which appears as a self-supporting flat and thin plate with surface dimensions of 1×1 mm and with a thickness of 10 μm, was subjected to photoluminescence excitation on its surface. The photoluminescence exciter source was a continuous laser beam with a wavelength of 488 nm (or, equivalently, 20492 $cm^{-1}$) and with a power of 5 mW. The incidence of the laser beam on the flat surface of the single crystal occurs at approximately 45° with respect to the plane that is normal to the surface, and the optical system for collecting the photoluminescence is on the same side of the specimen with respect to the laser beam and forms, with it, an angle of approximately 90°. Said irradiation conditions allow to effectively obtain photoluminescence from the specimen without however altering the optoelectronic and structural characteristics of the single crystal. The inventors stress that the arrangement of the above described experimental apparatus is merely a non-limitative example and that any other spatial arrangement can be suitable, so long as optical artifacts are not introduced in the measurement process and the specimen is not damaged reversibly or irreversibly. A bandpass optical filter is introduced in the photoluminescence collection line, which is formed by two quartz lenses with an aperture of 2.5 cm and a focal length of 7 cm, in order to eliminate the laser beam reflected by the single crystal. In this manner, only the photoluminescence emitted by the single crystal remains within the optical collection path and is focused on a quartz optical fiber which is coupled to a Hamamatsu OMA50 spectrum analyzer. Said spectrum analyzer, by having a diffraction grating and a CCD sensor, scatters the photoluminescence into its spectral components and associates with each energy value (which can be represented in $cm^{-1}$) the intensity, understood as a number which is proportional to the number of photons having that energy which are emitted by the single crystal. The result of this measurement is the nonpolarized photoluminescence spectrum shown in FIG. 4.

Spectral analysis shows that the most intense bands in the spectrum are at approximately 16550 $cm^{-1}$, while the peak at the highest energy is at approximately 18350 $cm^{-1}$. The distance between the two resonances is therefore 1800 $cm^{-1}$. Accordingly, the molecules are orientated at right angles to the surface of the single crystal. The result obtained by applying the method according to the present invention is found to match the one obtained by interpreting the X-ray diffraction spectrum. As shown in FIG. 3, the crystalline structure of hexathiophene obtained by X-ray diffraction on single crystals [7] indicates that in said individual crystals the molecules are orientated at right angles to the surface.

Example 2

An ultrathin film of hexathiophene, with a nominal thickness of 1 nm, was grown by sublimation in high vacuum with a base pressure of $10^{-7}$ mbar on a mica substrate. The mica substrate was exfoliated directly before being introduced in the growth chamber in order to eliminate any impurities present on the surface. The mica substrate was chosen for its characteristics of flatness and because it facilitates atomic-force microscopy analysis, which allows to obtain topographic images of the surface of the film. The deposition rate was 1.2 nm/minute and the substrate was kept, at 150° C. Once grown to the chosen nominal thickness of 1 nm, the film was lased in order to stimulate its nonpolarized photoluminescence, using the procedure and the instruments described in Example 1. The measured spectrum is plotted in FIG. 5.

Spectral analysis shows that the most intense band in the spectrum is at approximately 16900 $cm^{-1}$, while the highest-energy band is. at approximately 18350 $cm^{-1}$ as in the case of Example 1. The distance between the two resonances is therefore 1450 $cm^{-1}$. Accordingly, the molecules are parallel to the mica substrate. The inventors stress that the highest-energy band in the spectrum is always in the same position both in the single crystal of Example 1 and in the ultrathin film of the present example. This is due to the fact that the material involved is the same, i.e., hexathiophene, and that said band is typical of the material and does not depend on the orientation of the molecules with respect to the plane of observation. The position of the most intense vibrational bands instead changes depending on whether the molecules are parallel or perpendicular to the surface of the film. The result obtained by applying the method according to the present invention matches the one obtained by interpreting the topographic images recorded with atomic-force microscopy. It is in fact known [8] that in ultrathin films (thickness $\geq 1$ nm) grown by sublimation in the above specified conditions on flat and inert substrates such as mica, the oligothiophene molecules are parallel to the substrate. This result is achieved by analyzing the height of the profile of a section of the film with respect to the plane of the mica substrate. If the van der Waals dimensions of the hexathiophene molecule are known, by comparing said dimensions with the height of the profile of the film one can unambiguously determine whether the molecules are parallel or perpendicular to the substrate.

Clearly, the photoluminescence spectra due to molecules which are perpendicular or parallel to the surface (FIG. 4 and FIG. 5) are significantly different and easily allow to distinguish the two situations.

Example 3

A film of tetrathiophene, a homologue of hexathiophene but with four thiophene rings instead of six, was grown by high-vacuum sublimation with a base pressure of $10^{31\ 7}$ mbar on a substrate of highly orientated pyrolytic graphite (HOPG). The HOPG substrate was exfoliated directly before being introduced in the growth chamber in order to eliminate any impurities present on the surface. The HOPG substrate and the tetrathiophene were chosen for this example to replace, respectively, the mica and the hexathiophene in order to show that the present invention has a fully general validity both as regards the conjugated organic systems and the type of substrate. The deposition rate of the film was 1.2 nm/minute and was kept constant throughout evaporation. The temperature of the crucible with the material to be sublimated was monitored constantly and changed, if necessary, in order to maintain a constant rate of deposition on the substrate. The thickness of the film was constantly controlled by means of an indicator connected to a quartz microbalance calibrated for tetrathiophene and placed in the immediate vicinity of the substrate inside the growth chamber.

Figure 1:
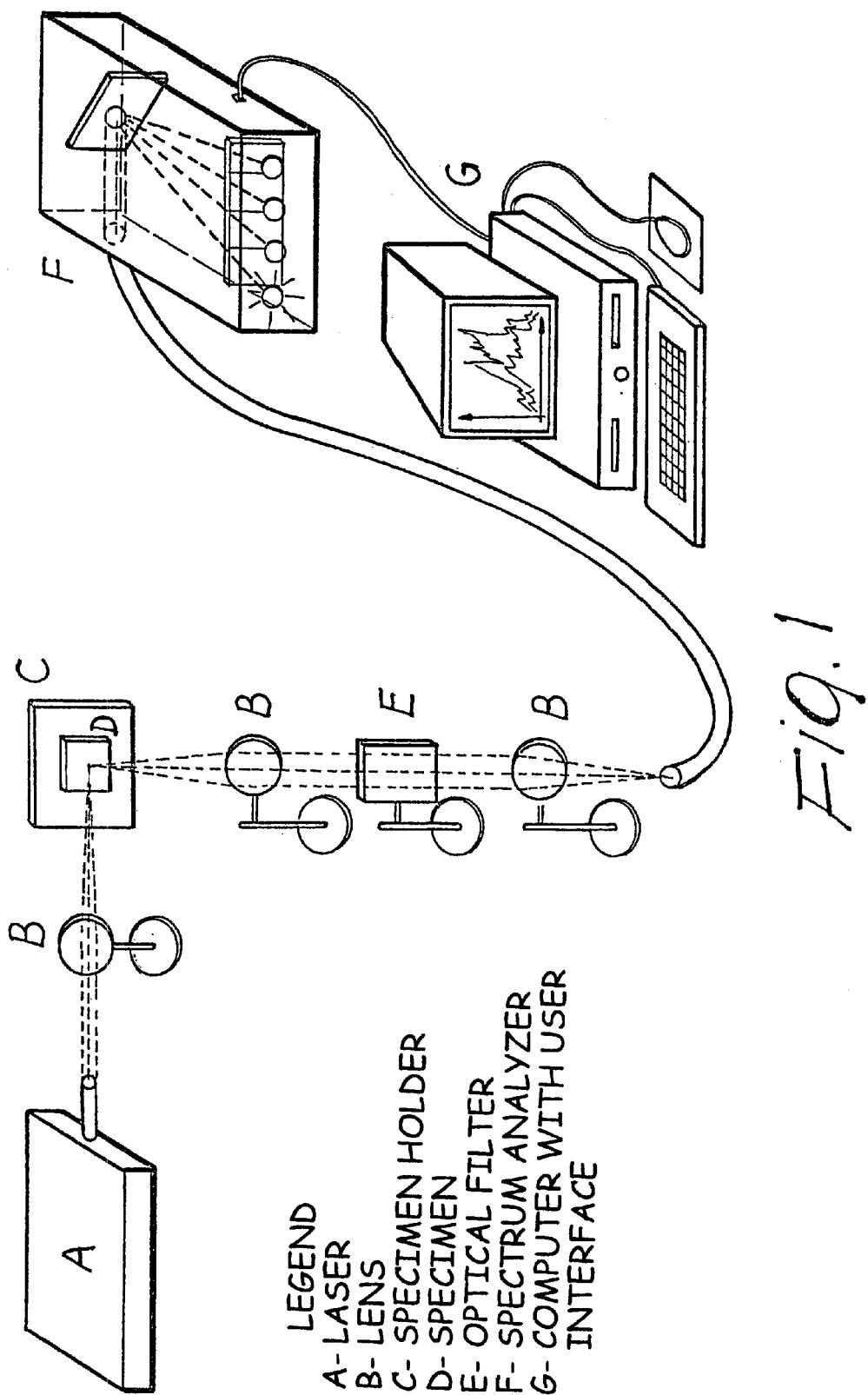
FIG. 1 is a schematic view of an apparatus for detecting ex post, after growth, molecular orientation in organic thin films with the method according to the present invention.
Figure 2:
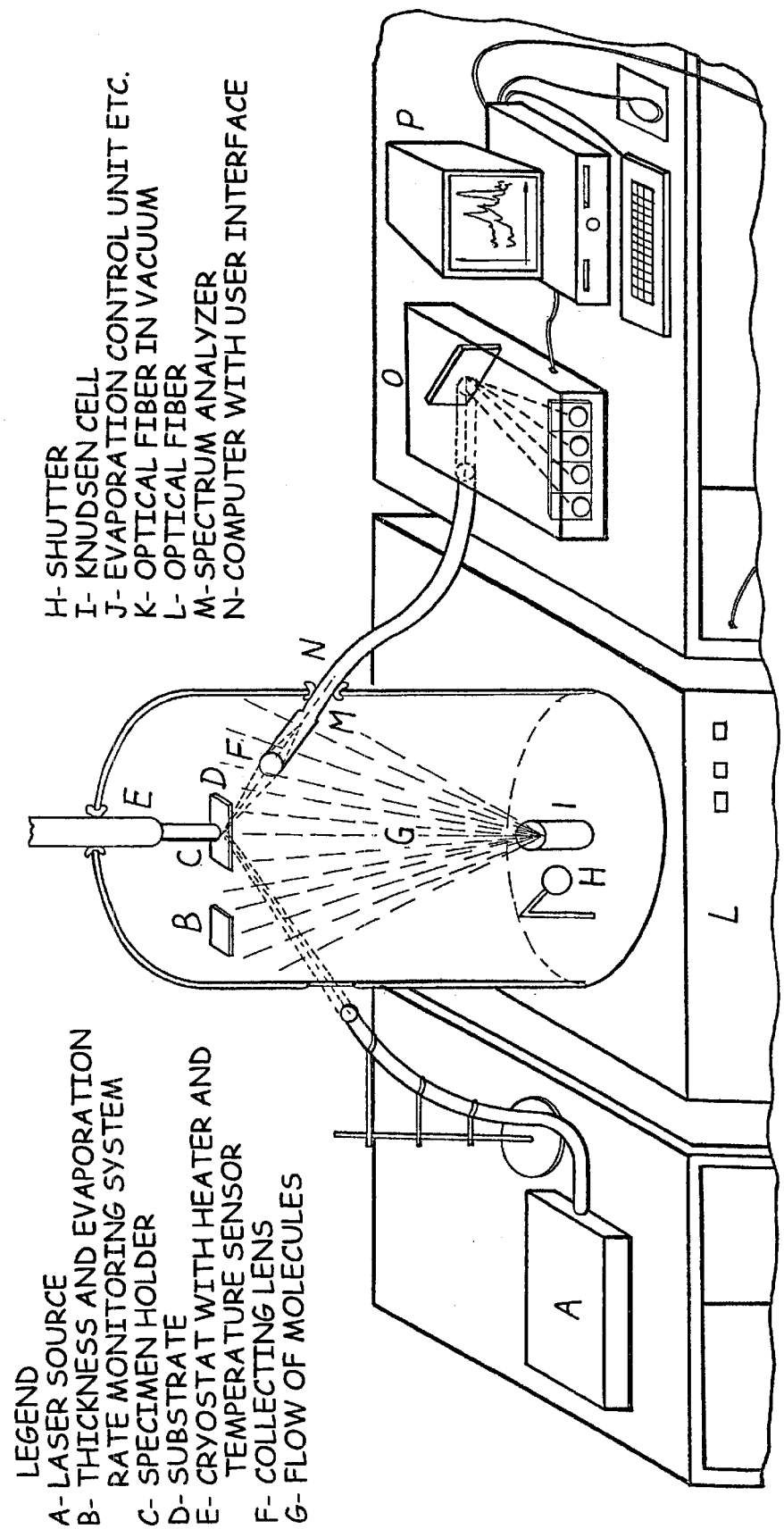
FIG. 2 is a schematic view of an apparatus for monitoring, during growth by vacuum sublimation, the orientation of the molecules on the substrate with the method according to the present invention.

During growth, and at different thickness values, the film was irradiated with a laser source in order to measure its photoluminescence. The experimental apparatus used is the one shown schematically in FIG. 2. It is fully similar to the one described in Example 1, except that it is coupled to the high-vacuum growth chamber and uses a laser beam wavelength of 457 nm (21882 cm$^{-1}$) instead of. 488 nm (20492 cm$^{-1}$). The use of a more energetic laser beam is necessary in order to stimulate photoluminescence of tetrathiophene, in which the optically active electronic transition is at higher energy with respect to hexathiophene. Consistently, the photoluminescence spectra of the film for thicknesses of 1 nm and 8 nm given in FIG. 6 have their highest-energy band at 21000 cm$^{-1}$, against the 18350 cm$^{-1}$ of hexathiophene.

The laser source stimulates the photoluminescence of the molecules that are present along all of its penetration depth, i.e., through the entire thickness of the film. As the thickness of the film increases, the photoluminescence spectrum changes according to the possible change of molecular orientation in the layers after the first one, changing the relative weight of the spectral components. In the spectrum measured when the thickness was 1 nm, the most intense band was in fact at 19500 cm$^{-1}$, i.e., spaced by 1500 cm$^{-1}$ from the electronic origin, while the bands at greater distance are much less intense. Accordingly, the molecules are predominantly orientated parallel to the substrate of HOPG.

When the film reached the thickness of 8 nm, the band at 19500 cm$^{-1}$ lost relative intensity in favor of bands at lower energy and therefore at a greater distance with respect to the electronic origin. Accordingly, the outermost molecular layers in an 8-nm film tend to orientate themselves at right angles to the substrate.

This result agrees with the experimental results obtained with various known methods, such as for example, atomic-force microscopy and X-ray diffraction, according to which the molecules are predominantly orientated at right angles to the substrate in films with thicknesses of more than 15–20nm.

It is thus possible to follow or monitor the evolution with thickness, in real time during growth, of the molecular orientation by measuring the nonpolarized photoluminescence spectrum. The dependence of the nonpolarized photoluminescence spectrum on the molecular orientation that the inventors have demonstrated is common to the entire family of conjugated organic systems.

Advantageously, real-time monitoring during growth or, in an equivalent manner, during manipulation can be used to change in real time the growth or manipulation conditions. For example, in the case of a film which grows with its molecules at right angles to the substrate, by increasing in real time the deposition rate and decreasing the temperature of the substrate it is possible to grow molecular layers in which the molecules are parallel to the substrate. By then returning to the original growth conditions, the film continues to grow with its molecules at right angles to the substrate. With the present invention, it is possible to monitor and guide growth processes similar to the one described herein.

It should be noted that analysis of molecular orientation does not necessarily require a high quantitative character. Relative and/or qualitative results are often satisfactory and can be applied in a wide range of industrial processes.

Further details on the exciter source, on the optical focusing system, on the optical system for collecting photoluminescence, on the source filtering system and on the photoluminescence spectrum analyzer are not included in the present explanation. All these elements are commonly known and used in optics.

The disclosures in Italian Patent Application No. MI99A002718 from which this application claims priority are incorporated herein by reference.

References

1. A. Dodabalapur, L. Torsi, H. E. Katz, Science 268.(1995) 270.
2. C. W. Tang and S. A. Van Slyke, Appl. Phys. Lett, 51 (1987) 913; J. H. Burroughes et al., Nature 347 (1990) 539.
3. Nobbs et al., Polymer, 15 (1974) 287.
4. Jarry et al., J. Poly. Sci., Poly. Phys., 18 (1980) 1879.
5. R. N. Marks et al., Phil. Trans. R. Soc. Lond. A 355 (1997) 763.
6. "Handbook of Oligo- and Polythiophenes" ed. by D. Fichou, Wiley-VCH, Weinheim 1999.
7. G. Horowitz et al., Chem. Mat., 7 (1995) 1337.
8. C. Taliani et al., in "Semiconducting polymers" ed. by G. Hadziioannou and P. F. van Hutten, Wiley-VCJ, Weinheim 1999.

What is claimed is:

1. A method for detecting the orientation of molecules which are anisotropic or have anisotropic behavior and for detecting the orientation of the unit crystalline cell in molecular layers, said method comprising the steps of:

exposing the molecular layer to luminescence excitation;

measuring the nonpolarized luminescence spectrum produced by said luminescence excitation;

spectral and vibrational analysis of said luminescence spectrum in order to determine the orientation of the molecules.

2. The method according to claim 1, wherein said luminescence excitation is a photoluminescence excitation or an electroluminescence excitation.

3. The method according to claim 1, wherein said molecular layer is in film form, substantially in the form of a thin film on a substrate.

4. The method according to claim 1, wherein said molecular layer is not supported.

5. The method according to claim 2, wherein said molecular layer is constituted by a continuous surface or by spatially separate domains, and in that the luminescence excitation occurs with a spatial resolution which is suitable to locally excite the continuous surface or each one of said domains individually.

6. The method according to claim 1, wherein said spectral and vibrational analysis implies the detection of bands related to vibronic transitions associated with a perpendicular orientation of the molecules and of bands related to vibronic transitions associated with a parallel orientation of the molecules with respect to the surface of the film or of the molecular layer.

7. The method according to claim 6, wherein the spectral and vibrational analysis furthermore comprises an evaluation of relative weights of the perpendicular and parallel molecular orientations in order to determine the predominant molecular orientation and optionally of the relative weight of the perpendicular or parallel orientation with respect to the predominant orientation.

8. The method for monitoring in real time the molecular orientation in thin films during the growth of said thin films, said method comprising detection of the orientation of the molecules of the film by application of a method according to claim 1.

9. A method for monitoring in real time, or for detecting ex post, the effect of manipulation or nanomanipulation on molecular orientation in films, comprising detection of the molecular orientation by application of a method according to claim 1 during or, respectively, after manipulation or nanomanipulation of the film.

10. A method for monitoring the variation over time of the structural properties of films due to deterioration by aging, or due to operation in the case of optoelectronic devices based on said films, said method comprising detection of the orientation of the molecules in said films by applying a method according to claim 1.

11. An apparatus for detecting the orientation of molecules in molecular layers by means of a method according to claim 1, said apparatus being constituted by the following elements:

a luminescence exciter source, particularly for example a laser;

an optional system for focusing the exciter source;

an optical system for collecting the luminescence generated by the specimen;

an optional system for filtering the exciter source;

an analyzer of luminescence spectra suitable to determine the orientation of the molecules;

an interface with the user, suitable to indicate the orientation of the molecules and optionally provide the relative weights of the various orientations detected with respect to the dominant orientation.

12. The apparatus according to claim 11, further comprising a system for varying in real time the growth conditions, suitable to act according to the result of the determination of the molecular orientation and achieve a growth target when it is coupled to a film growth system.

13. The apparatus according to claim 11, further comprising a system for varying in real time the manipulation conditions, suitable to act according to the result of the determination of the molecular orientation and achieve a manipulation target when it is coupled to a film manipulation system.

14. An apparatus according to claim 11, further comprising a system for focusing and shifting the beam of the exciter source in order to allow to determine the orientation of the molecules in different points of a continuous surface or of a surface constituted by domains.

* * * * *